(12) United States Patent
Komatsu et al.

(10) Patent No.: US 6,490,481 B1
(45) Date of Patent: Dec. 3, 2002

(54) LIVING BODY MEASURING APPARATUS

(75) Inventors: Yoshichika Komatsu, Senboku-Machi (JP); Yoshitsugu Sasaki, Wako (JP)

(73) Assignee: Tanita Corporation, Tokyo (JP)

( * ) Notice: Subject to any disclaimer, the term of this patent is extended or adjusted under 35 U.S.C. 154(b) by 34 days.

(21) Appl. No.: 09/684,792

(22) Filed: Oct. 10, 2000

(30) Foreign Application Priority Data

Oct. 12, 1999 (JP) .......................................... 11-290035

(51) Int. Cl.$^7$ ................................................ A61B 5/05
(52) U.S. Cl. ...................................... 600/547; 600/372
(58) Field of Search ................................ 600/547, 372, 600/384, 546, 554; 177/25.12, 25.18, 245

(56) References Cited

U.S. PATENT DOCUMENTS

| | | | | |
|---|---|---|---|---|
| 5,335,667 A | * | 8/1994 | Cha et al. ..................... | 600/547 |
| 5,449,000 A | * | 9/1995 | Libke et al. .................. | 600/547 |
| 5,483,970 A | * | 1/1996 | Rosenberg ................... | 600/546 |
| 5,720,296 A | * | 2/1998 | Cha ............................ | 600/554 |
| 5,819,741 A | * | 10/1998 | Karlsson et al. ............. | 600/523 |
| 6,004,312 A | * | 12/1999 | Finneran et al. ............. | 600/546 |
| 6,280,396 B1 | * | 8/2001 | Clark .......................... | 600/547 |
| 6,308,096 B1 | * | 10/2001 | Masuo ........................ | 600/547 |

FOREIGN PATENT DOCUMENTS

| | | | |
|---|---|---|---|
| JP | 07012635 A | * | 1/1995 |
| JP | 09192113 | | 7/1997 |
| WO | WO 97/01303 | | 1/1997 |

OTHER PUBLICATIONS

European Search Report dated Jan. 22, 2001.
"Evaluation of Segmental Bioelectrical Impedance Analysis (SBIA) for Measuring Muscle Distribution", Kichul Cha, Ph.D., et al.; J ICHPER. SD–ASIA., p.11–14, 1997.

* cited by examiner

Primary Examiner—Kevin Shaver
Assistant Examiner—Charles Marmor, II
(74) Attorney, Agent, or Firm—McDermott, Will & Emery

(57) ABSTRACT

A living body measuring apparatus includes a plurality of electrodes each of which is structured to make contact with a part of a living body; a current source connected to the electrodes; a voltage measuring unit connected to the electrodes; a control unit connected to the current source and the voltage measuring unit; and a display unit connected to the control unit. The control unit instructs the display unit to display the part of the living body to which an electric current is fed to the current source via the associated electrodes. The control unit further instructs the display unit to display the part of the living body of which voltage is measured by the voltage measuring unit on the associated electrodes.

9 Claims, 20 Drawing Sheets

FIG. 6a

ENTER CLOTHES WEIGHT  [RETURN]

CLOTHES WEIGHT  Kg  [FORWARD]

| 7 | 8 | 9 |
| 4 | 5 | 6 |
| 1 | 2 | 3 | [ERASE]
| 0 | . | [BACK]

FIG. 6b

ENTER CLOTHES WEIGHT  [RETURN]

CLOTHES WEIGHT  1.5kg  [FORWARD]

| 7 | 8 | 9 |
| 4 | 5 | 6 |
| 1 | 2 | 3 | [ERASE]
| 0 | . | [BACK]

FIG. 6c

MEASUREMENT OF BODY
WEIGHT IS GOING TO START    [RETURN]
GET ON THE WEIGHT
METER WITH BARE FEET        [FORWARD]

CLOTHES WEIGHT TO
BE SUBTRACTED:

$$-1.5 \text{kg}$$

FIG. 6d

[RETURN]

BODY WEIGHT MEASURED IS: [FORWARD]

$$56.0 \text{kg}$$

PROCEED NEXT STEP AND
ENTER THE NECESSARY ITEMS

FIG. 6e

ENTER BODY FEATURE AND SEX

[RETURN]
[FORWARD]

- MALE STANDARD TYPE
- FEMALE STANDARD TYPE
- MALE SLENDER TYPE
- FEMALE SLENDER TYPE

FIG. 6f

ENTER AGE

AGE:　　　　YEARS OLD

[RETURN]
[FORWARD]

| 7 | 8 | 9 | |
|---|---|---|---|
| 4 | 5 | 6 | |
| 1 | 2 | 3 | ERASE |
|   | 0 | . | BACK |

FIG. 7a

ENTER HEIGHT   [RETURN]

HEIGHT: _____ cm   [FORWARD]

[7] [8] [9]

[4] [5] [6]

[1] [2] [3] [ERASE]

[0] [.] [BACK]

FIG. 7b

CONFIRM DATA THAT YOU   [RETURN]
ENTERED AND DEPRESS
"START" KEY

["START"]  ["STOP"]

DATA (IF CORRECTION IS NECESSARY
DEPRESS "RETURN" KEY)

| BODY WEIGHT: 56.0kg | BODY FEATURE: MALE, STANDARD |
| AGE: 35 YEARS OLD | HEIGHT: 165cm |

FIG. 9a

| MEASUREMENT RESULT DISPLAY | DISPLAY SELECTOR | PART SELECTOR | DISPLAY TERMINATION | |
|---|---|---|---|---|
| BODY FEATURE: STANDARD | SEX:MALE | AGE:XX YEARS OLD | HEIGHT:YYYcm | |
| BODY WEIGHT: 56.0kg | STANDARD WEIGHT: 54.0kg | BMI 23.7 | CORPULENCE DEGREE:7.7% | |
| WHOLE BODY FAT PERCENTAGE:20.5% | | | BODY FAT PERCENTAGE: 17.0~23.0% | STANDARD LIMITS |
| BODY FAT AMOUNT: 18.0kg | WEIGHT EXCLUDING BODY FAT:52.0kg | | BODY FAT AMOUNT:9.9~14.4kg | |

| | RIGHT ARM | RIGHT LEG | LEFT ARM | LEFT LEG | HEAD AND MAIN BODY |
|---|---|---|---|---|---|
| IMPEDANCE | | | | | |
| PARTIAL BODY FAT PERCENTAGE | | | | | |
| PARTIAL BODY FAT AMOUNT | | | | | |
| PARTIAL MUSCLE AMOUNT | | | | | |

DEPRESS "PRINT" KEY IF YOU NEED     PRINT

US 6,490,481 B1

LIVING BODY MEASURING APPARATUS

BACKGROUND OF THE INVENTION

1. Field of the Invention

The present invention relates to a living body measuring apparatus for measuring the condition of each part of a living body.

2. Description of the Prior Art

Many of the living body measuring apparatus currently available provide a function for indicating the passed time interval or the remaining time interval for the measurement or for displaying a simplified chart to indicate the progress of measurement by a bar code and the like.

Such conventional living body measuring apparatus generally indicate the entire progress of measurement. However, in more complicated measuring apparatus for measuring each of the parts of the living body in turn, due to longer time period of, for example, a few minutes required for measurement, it is unknown for a person under test what part of the body is now being measured. Therefore, the person under test feels a significantly longer period of time for the measurement than actual. In the extreme case it may happen that the person under test feels some misgivings about whether the measurement is truly proceeding or not, while seeing the display of passed time interval, and as the result, he stops the measuring apparatus, irrespective of in the course of measurement.

The present invention solves such problems in the prior art by providing a new and improved measuring apparatus in which a person under test is not aware of progress in time for measurement and he can know which parts of the body are now being measured.

SUMMARY OF THE INVENTION

In view of the above, the present invention provides a living body measuring apparatus, comprising:

a plurality of electrodes each of which is structured to make contact with a part of a living body;

a current source connected to said electrodes;

a voltage measuring unit connected to said electrodes;

a control unit connected to said current source and said voltage measuring unit; and a display unit connected to said control unit, whereby said control unit instructs said display unit to display the part of the living body to which an electric current is fed by said current source via the associated electrodes.

The living body measuring apparatus further comprises a switching unit, whereby said switching unit selects which electrodes the electric current is fed to. The control unit changes over the part of the body displayed on the display unit in response to the operation of said switching unit.

In another aspect the present invention provides a living body measuring apparatus, comprising:

a plurality of electrodes each of which is structured to make contact with a part of a living body;

a current source connected to said electrodes;

a voltage measuring unit connected to said electrodes;

a control unit connected to said current source and said voltage measuring unit; and a display unit connected to said control unit, whereby said control unit instructs said display unit to display the part of the living body of which voltage is measured by said voltage measuring unit on the associated electrodes.

The living body measuring apparatus further comprises a switching unit, whereby said switching unit selects the electrodes on which the voltage is measured. The control unit changes over the part of the body displayed on the display unit in response to the operation of said switching unit.

Further according to the present invention the parts of the living body that the measurement has already been done or is now being performed or is to be performed next may be displayed on the display unit with a solid line, a broken line or a point-dot line. In another embodiment the parts of the living body that the measurement is now being performed may be displayed on the display unit with a broken line that moves in one way. In further embodiment all parts of the living body may be displayed on the display unit in rectangular blocks and some of the blocks corresponding to the parts that the measurement is now being performed may be displayed with a dark shading.

BRIEF DESCRIPTION OF THE DRAWINGS

Now, the present invention will be described in more detail with reference to the accompanying drawings, in which

FIGS. 6a–6f, 7a–7f, 8a–8e, 9a–9e and 10a–10e show one embodiment of display screens of a display unit;

DESCRIPTION OF THE PREFERRED EMBODIMENTS

A measuring apparatus according to the present invention operates to switch a plurality of electrodes by a switch unit and to display a part of a body on which the measurement is now being performed.

The measurement apparatus further operates to display the parts of the body on which the measurement has already been done and is now being performed.

The measurement apparatus further operates to display the parts of the body on which the measurement has already been done, is now being performed and is to be performed next.

Figure 1:
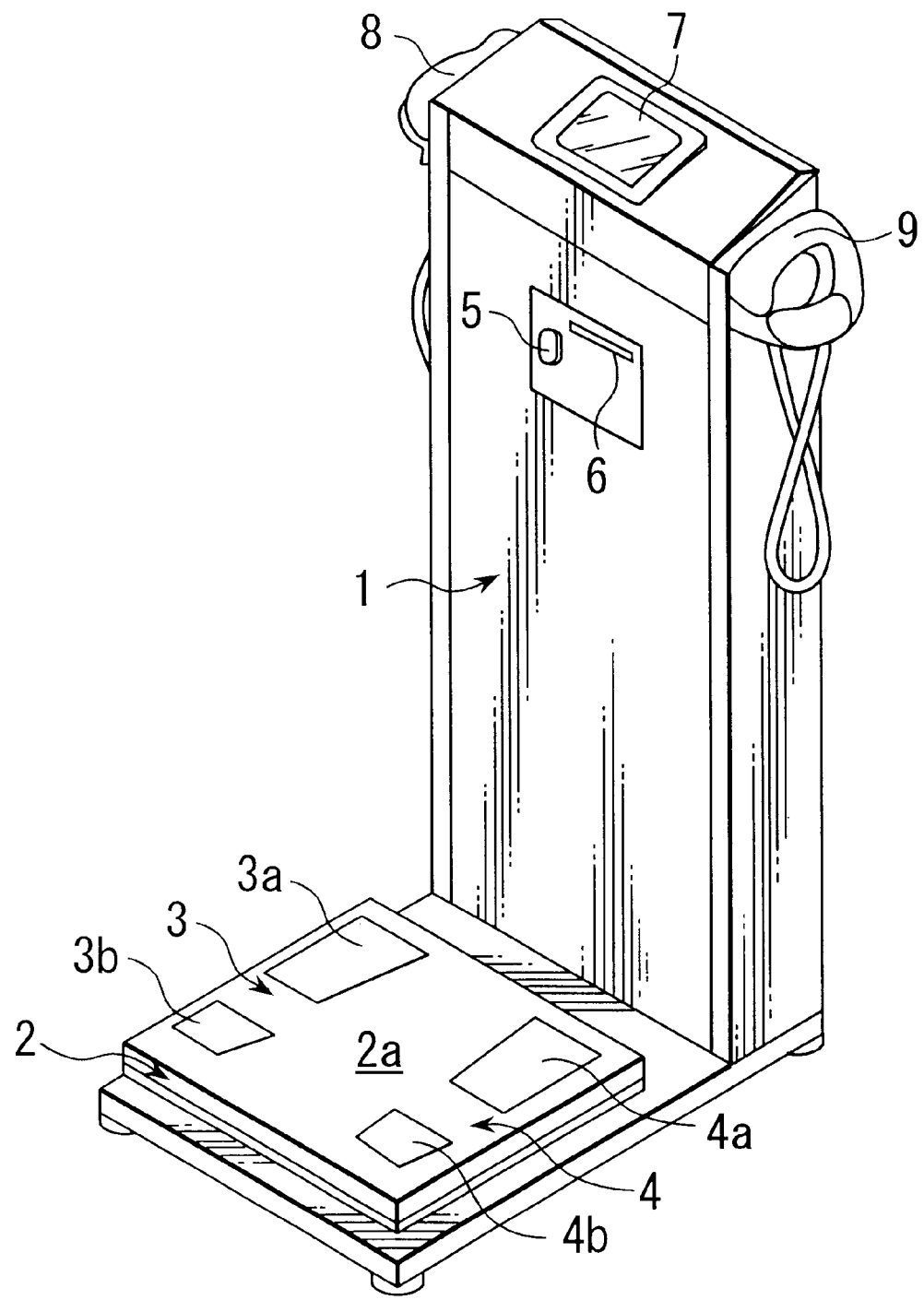
FIG. 1 is a perspective view representing a measuring apparatus according to the present invention.

FIG. 1 is a perspective view representing a measuring apparatus 1 according to the present invention. The measuring apparatus 1 is in the form of a letter "L" consisting of a vertical portion and a horizontal portion. A conventional weight meter 2 is mounted on the horizontal portion of the apparatus 1 for measuring the body weight of a person under test. The weight meter 2 has foot electrodes 3 and 4 provided on the top surface thereof for making contact with the soles of left and right feet of the person under test. The foot electrodes 3 and 4 are provided with current feeding electrodes 3a, 4a and voltage measurement electrodes 3b, 4b. The measuring apparatus 1 further includes a power switch 5 and a printer 6 mounted on the front surface thereof. In addition, the measuring apparatus 1 includes a display and input unit 7 made from a touch panel type LCD display mounted on the top surface thereof, and left and right hand electrodes 8, 9 held at upper left and right opposite sides of the apparatus. The left and right hand electrodes 8 and 9 are provided with current feeding electrodes 8a, 9a and voltage measurement electrodes 8b, 9b. The hand electrodes 8 and 9 are well known in the art, as found in the hand-held body fat measuring unit currently available in the market. Therefore there is no need for further description for such hand electrodes.

Figure 2:
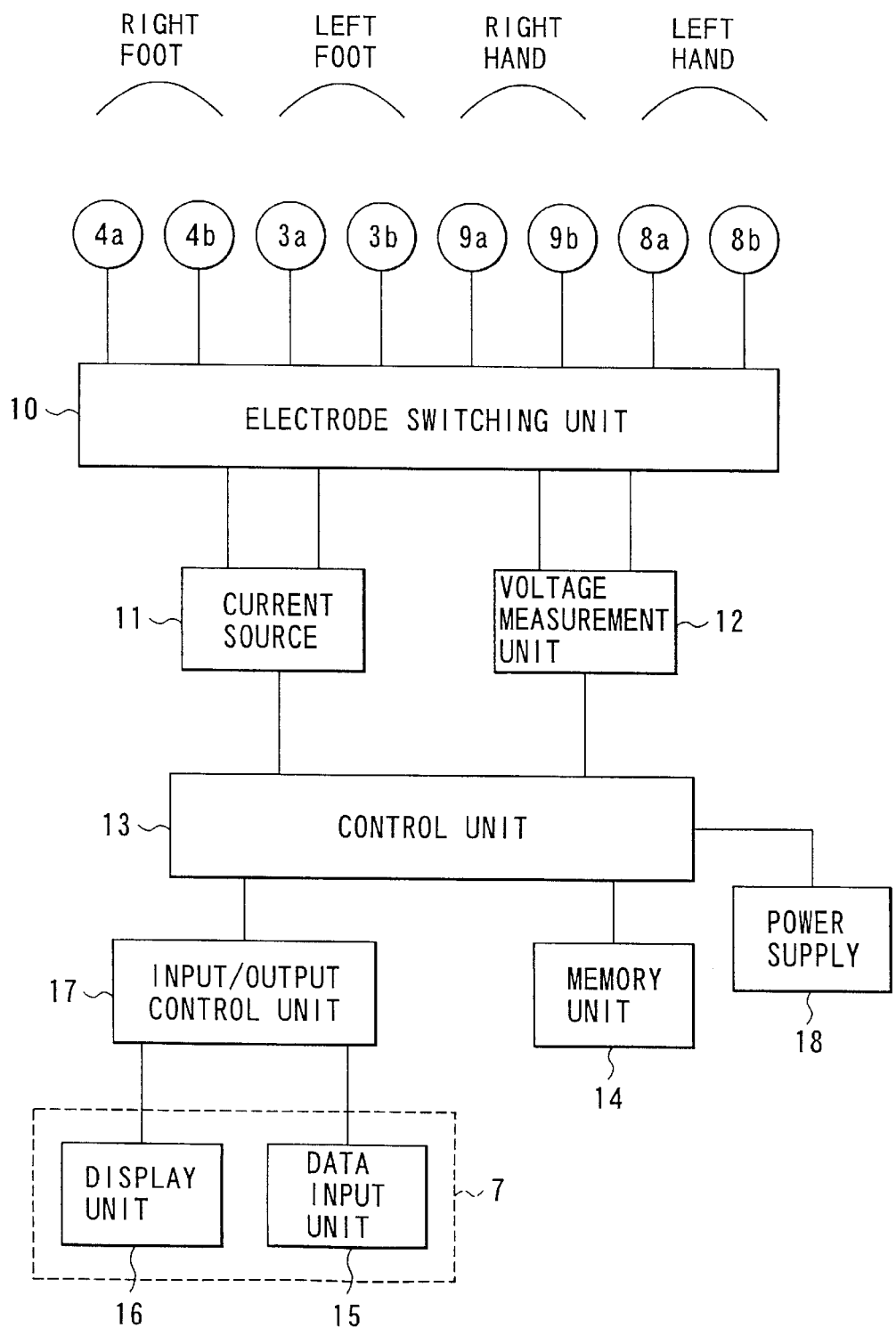
FIG. 2 is an electrical block diagram representing the measuring apparatus.

FIG. 2 is an electrical circuit diagram of the measuring apparatus 1. Referring to FIG. 2, the left and right foot and hand electrodes 3a, 3b, 4a, 4b, 8a, 8b, 9a, 9b are connected to an electrode switch 10. The electrode switch 10 is then connected to a control unit 13 via a current source 11 and a voltage measuring unit 12. The control unit 13 incorporates a microcomputer and a memory unit 14 is connected to the control unit 13. The display and input unit 7 in FIG. 1 is electrically divided into a data input unit 15 and a display unit 16, and they are connected to the control unit 13 via an input/output control unit 17 acting as a controller therefor. In addition, a power supply 18 is included for feeding power to the control unit 13 and other units.

Figure 3:
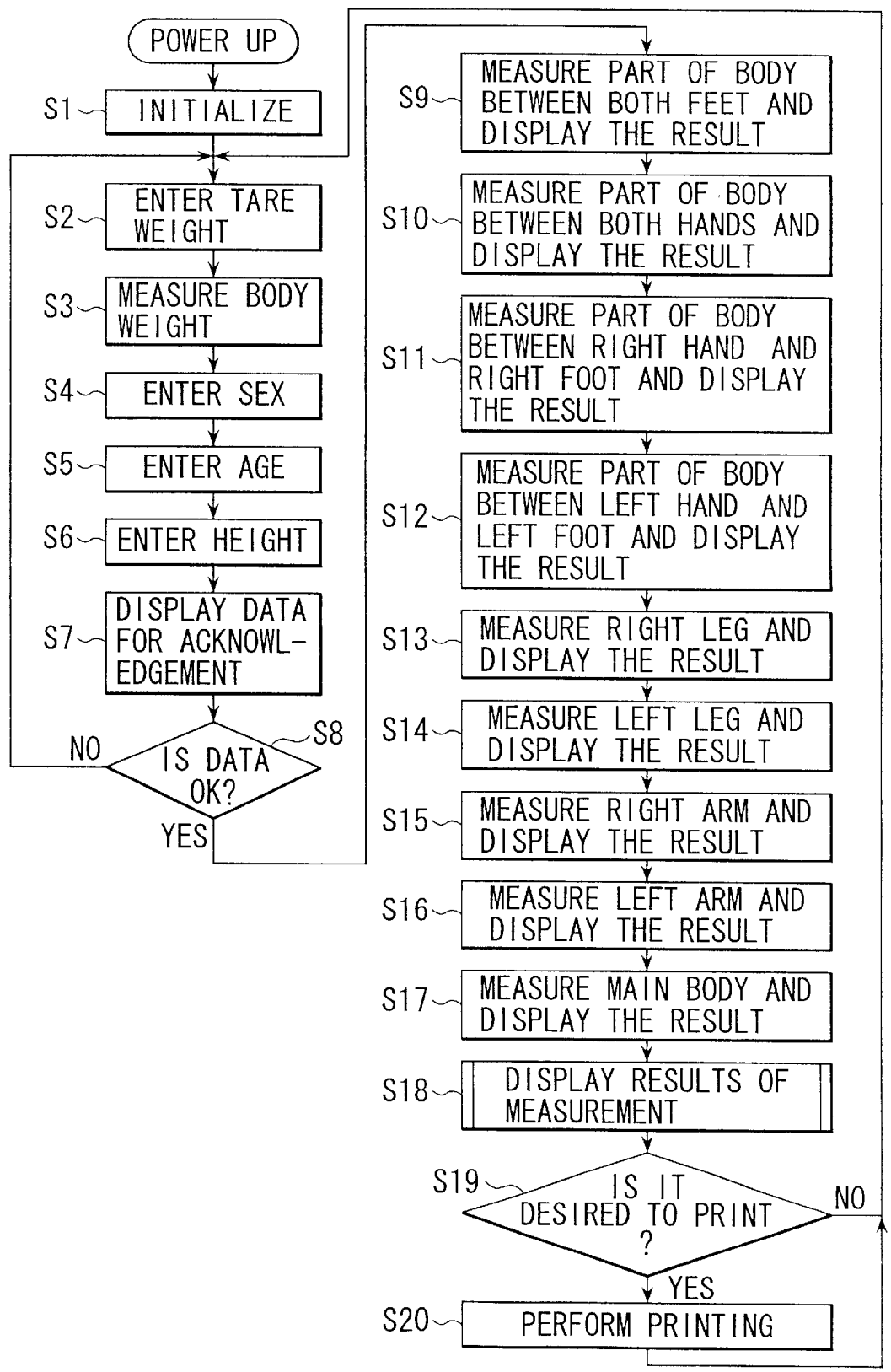
FIGS. 3, 4 and 5 are flow charts each representing a sequence of operation of the measuring apparatus.

Then an operation of the measuring apparatus 1 according to the present invention will be described hereunder with reference to flow charts of FIGS. 3, 4 and 5, as well as display screens of FIGS. 6a–6f, 7a–7f, 8a–8e, 9a–9e and 10a–10e. At first the power switch 5 of the measuring apparatus 1 is turned ON. Then in step S1 all the electrical circuits are initialized and in step S2 the routine enters a clothes weight input mode, as shown in FIG. 6a. In this mode, a message for prompting the person to enter the weight of clothes that he wears is indicated on the display unit 16, in addition to a picture of keyboard for entering this clothes weight. When the person enters the weight of his clothes, for example, 1.5 Kg using the numerical keys of the keyboard, the value of clothe weight is displayed, as shown in FIG. 6b. Then the person depresses a "Forward" key to proceed to step S3. However, if the person found that the clothes weight entered is wrong, he can use an erasing key to erase all the numbers at a time. Or alternatively the person may use a back key to erase the numbers one at a time. Then he can re-enter the correct clothes weight value.

In step S3 the routing enters a body weight measurement mode. As shown in FIG. 6c, a message for prompting the person to get on the top surface 2a of the weight meter 2 with bare feet is indicated on the display screen. In addition, the clothes weight already entered in step S2 is also shown, but with "minus (-) symbol added, to indicate that the clothes weight is to be subtracted from the measured body weight. When the person gets on the top surface 2a of the weight meter 2, the body weight of the person is measured by the weight meter 2 and the value of the body weight is indicated, as shown in FIG. 6d. A message for prompting the person to proceed to the next step or step S4 is additionally displayed on the screen. When depressing the "Forward" key, then the person can enter his physical feature and sex, as shown in FIG. 6e. If the person depresses a "Male, Standard type" key, for example, the routine proceeds to step S5 wherein the age of the person is entered. Then the person enters his age using the numerical keys, as shown in FIG. 6f. When depressing the "Forward" key, the routine proceeds to Step S6 wherein the height of the person is entered. Then the person enters his height using the numerical keys, as shown in FIG. 7a. When depressing the "Forward" key, the routine proceeds to step S7 wherein all the data for the person measured and entered in steps S3 to S6 are displayed on the display unit 16, as shown in FIG. 7b. In step S8, if the person depresses, a "Return" or a "Stop" key, the routine returns to step S2 for performing the measurement and input operation once again. When the person depresses a "Start" key, however, the routine proceeds to step S9 to start the measurement of the parts of the person under test.

Figure 7C:
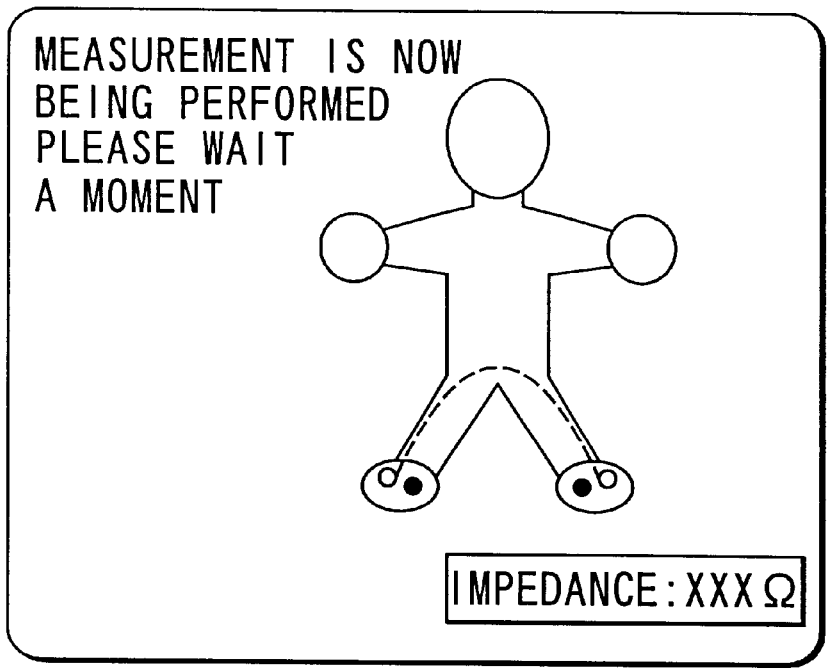
Figure 7D:
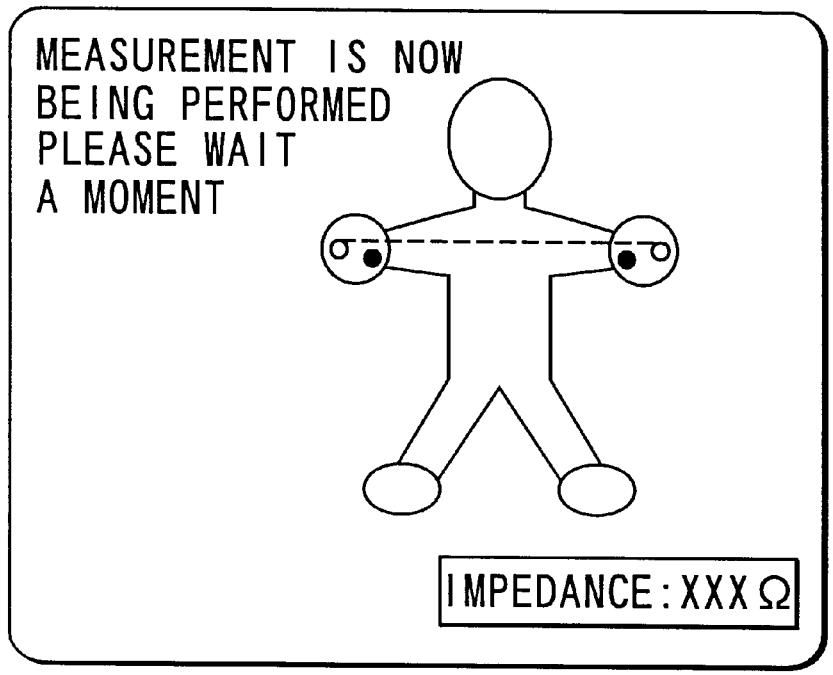
Figure 7E:
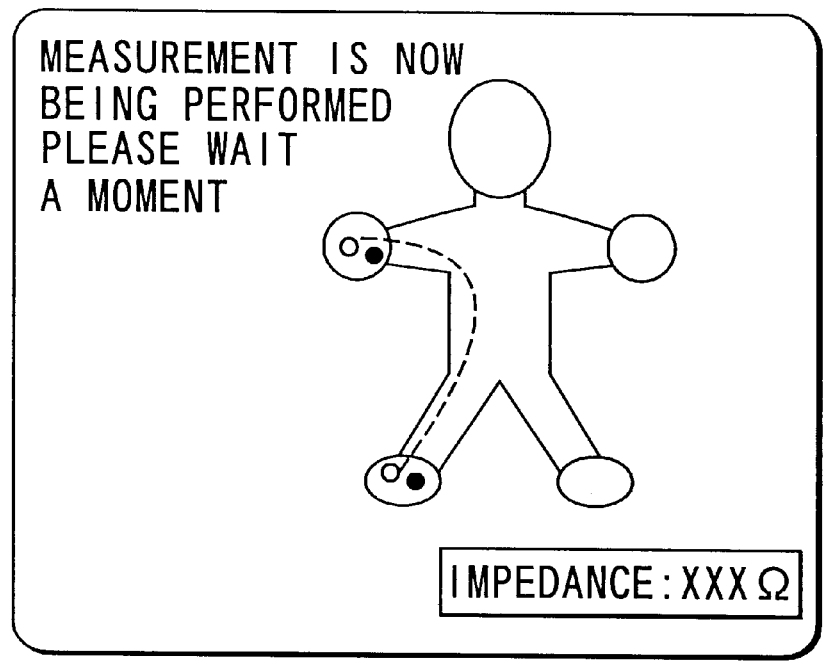
Figure 7F:
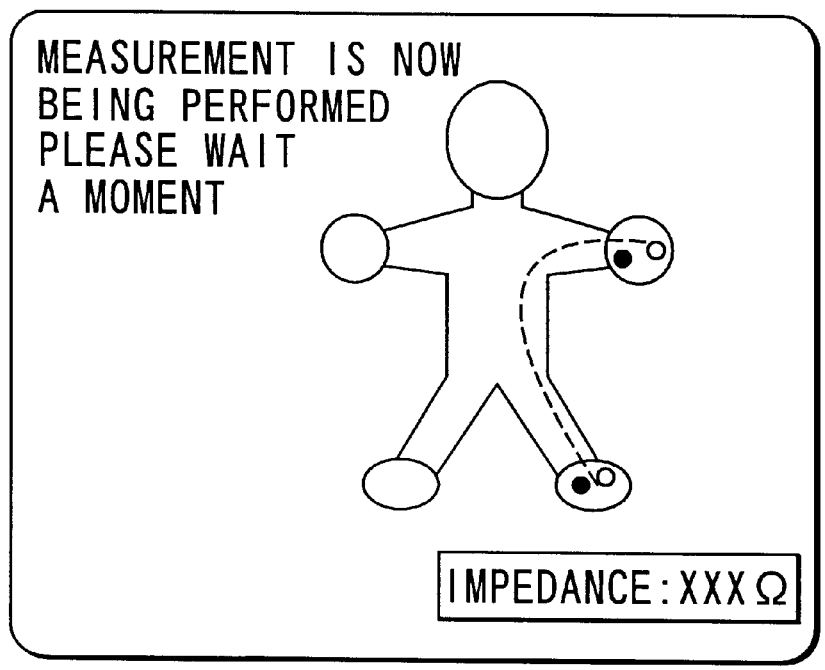

In step S9 the electrode switch 10 is operated in response to the command from the control unit 13 so that the current source 11 feeds AC current to the electrodes 3a, 4a and the voltage measurement unit 12 measures the voltage across the electrodes 3b, 4b. The measured voltage is fed to the control unit 13 for calculating the electrical impedance. As shown in FIG. 7c, a whole body model of the person under test, and the part of the body is now being measured are displayed on the display unit 16, together with the electrical impedance calculated. In this connection black dots in the whole body model represent the positions of the body, i.e., both feet of the person, into which the electrical current is introduced from the current source 11 via the associated electrodes. On the other hand white dots represent the positions of the body, i.e., both feet of the person, of which voltage is measured on the associated electrodes. In addition a broken line represents the part of the body between both feet for which the measurement is now being performed. Such indication of the current introduction points and the voltage measurement points affords a feel of security for the person and makes him unaware of the time that has passed for the measurement. After completion of the measurement, the routine proceeds to step S10. In this step the part of the body between both hands is measured by feeding the electric current to the electrodes 8a, 9a and measuring the voltage across the electrodes 8b, 9b, as shown in FIG. 7d. In this case the black dots representing the current introduction points and the white dots representing the voltage measurement points are placed in both hands of the whole body model. In addition the broken line represents the part of the body between both hands for which the measurement is now being measured. Then in step S11 the part of the body between the right hand and the right foot is measured by feeding the electric current to the electrodes 4a, 9a and measuring the voltage across the electrodes 4b, 9b, as shown in FIG. 7e. Thereafter, in step S12 the part of the body between the left hand and left foot is measured by feeding the electric current to the electrodes 3a, 8a and measuring the voltage across the electrodes 3b, 8b, as shown in FIG. 7f.

Figure 8A:
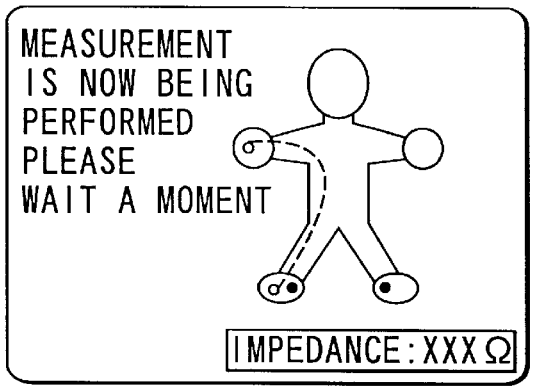

In step S13 the right leg of the person is measured by feeding the electric current to the electrodes 3a, 4a and measuring the voltage across the electrodes 9b, 4b, as shown in FIG. 8a. In this connection the electric current is introduced into the points indicated by the black dots, i.e., both feet of the person. Then the voltage across the right hand and the right foot is measured, as shown by white dots and the broken line, to measure the voltage on the right leg of the person. The resultant voltage value is divided by the electric current value to produce the impedance for the right leg.

Figure 8B:
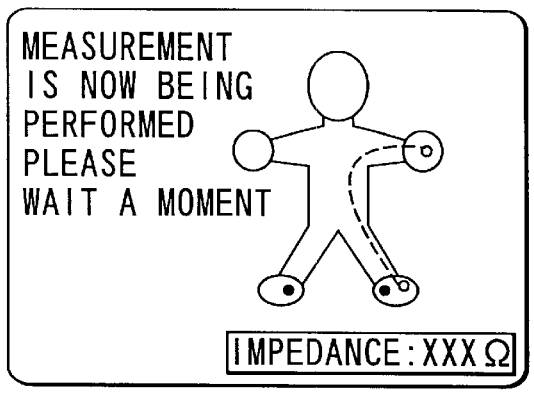

In step S14 the left leg of the person is measured by feeding the electric current to the electrodes 4a, 3a and measuring the voltage across the electrodes 3b, 8b, as shown in FIG. 8b. In this case the electric current is introduced into the points indicated by the black dots, i.e., both feet of the person. Then the voltage across the left hand and the left foot is measured, as shown by white dots and the broken line, to measure the voltage on the left leg of the person. The resultant voltage value is divided by the electric current value to produce the impedance for the left leg.

Figure 8C:
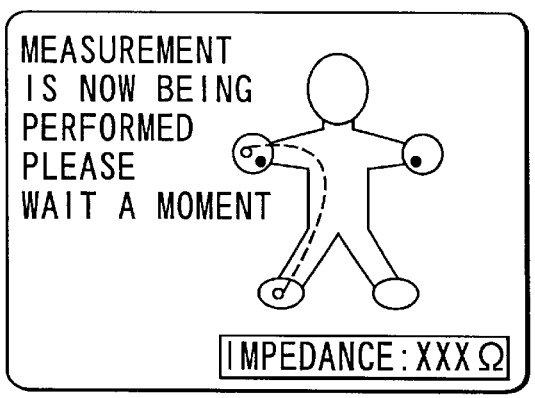

In step S15 the right arm of the person is measured by feeding the electric current to the electrodes 9a, 8a and measuring the voltage across the electrodes 4b, 9b, as shown in FIG. 8c. In this case the electric current is introduced into the points indicated by the black dots, i.e., both hands of the person. Then the voltage across the right hand and the right foot is measured, as shown by white dots and the broken line, to measure the voltage on the right arm of the person. The resultant voltage value is divided by the electric current value to produce the impedance for the right arm.

Figure 8D:
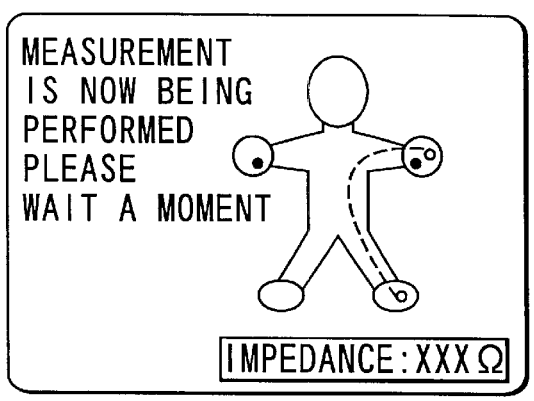

In step S16 the left arm of the person is measured by feeding the electric current to the electrodes 8a, 9a and measuring the voltage across the electrodes 8b, 3b, as shown in FIG. 8d. In this case the electric current is introduced into the points indicated by the black dots, i.e., both hands of the person. Then the voltage across the left hand and the left foot is measured, as shown by white dots and the broken line, to measure the voltage on the left arm of the person. The resultant voltage value is divided by the electric current value to produce the impedance for the left arm.

Figure 8E:
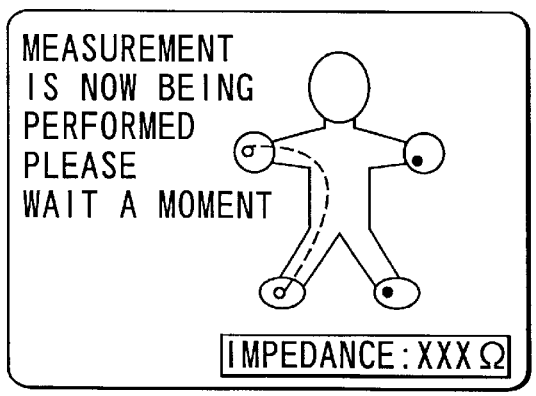

In step S17 the main body of the person is measured by feeding the electric current to the electrodes 8a, 3a and measuring the voltage across the electrodes 9b, 4b, as shown in FIG. 8e. In this case the electric current is introduced into the points indicated by the black dots, i.e., the left hand and the left foot of the person. Then the voltage across the right hand and the right foot is measured, as shown by white dots and the broken line, to measure the voltage on the main body of the person. The resultant voltage value is divided by the electric current value to produce the impedance for the main body.

After completion of the measurement for each part of the body, the results of the measurement are displayed in step S18. Then in step S19 the decision is made whether the print key is depressed or not. If not, the routine returns to step S2, but if so, the routine proceeds to step S20 wherein the printer 6 is operated to print. Thereafter, the routine returns to step S2.

Figure 4:
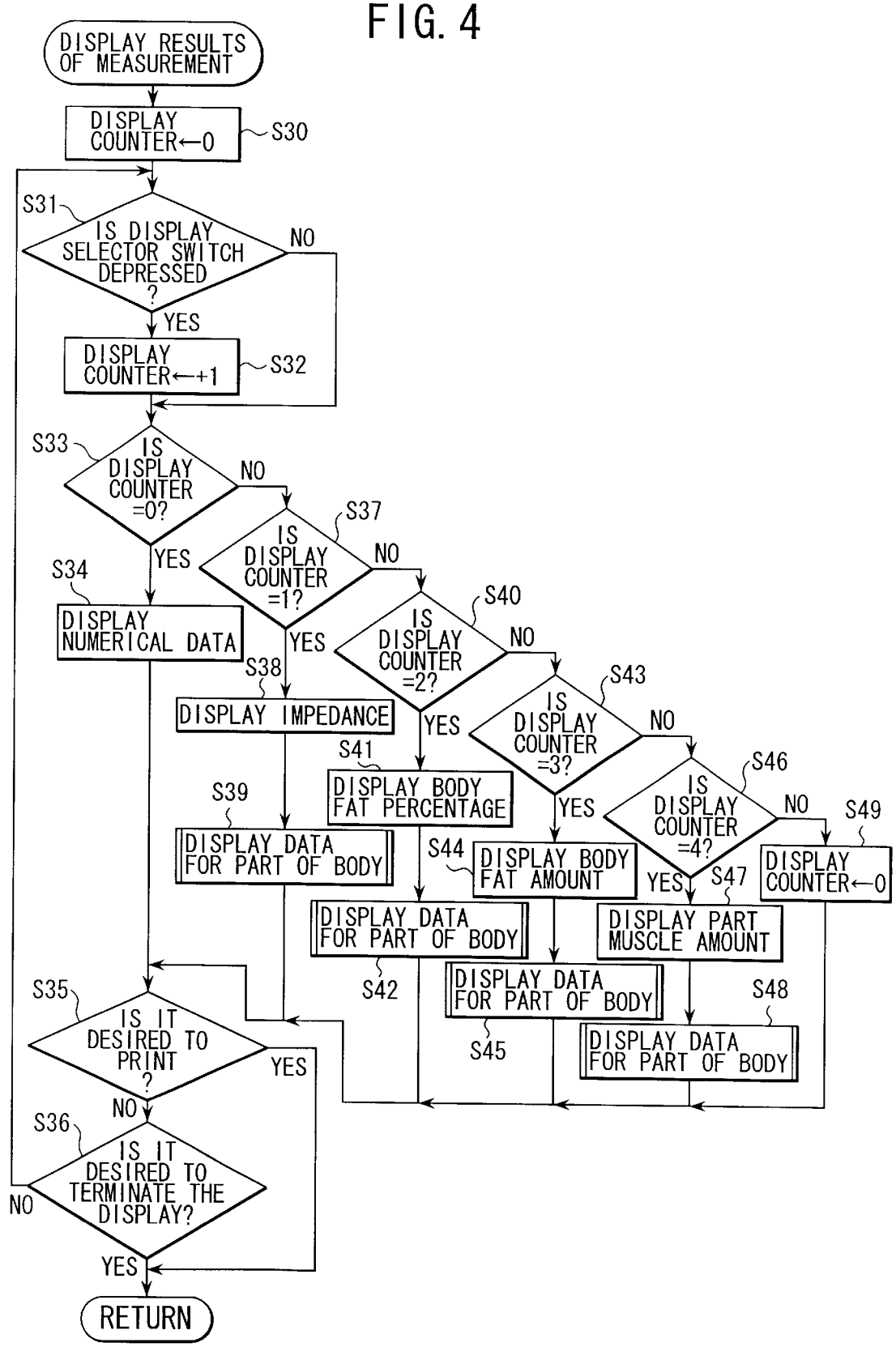

Referring to FIG. 4, the subroutine for displaying the measurement results in step S18 will be described in more detail. In step S30 a display counter in the control unit 13 is reset to "0" and in step S31 the decision is made whether a display selector switch as described latter is depressed or not. Initially the answer is "No", and therefore, the subroutine proceeds to step S33. In step S33 because of the display counter reset to "0" in step S30 the answer is "Yes" and then the subroutine proceeds to step S34. In this step the numerical data for the person under test, including the body weight, the whole body fat percentage, the weight excluding body fat, the impedance of each part, the partial body fat percentage, the partial body fat amount and the partial muscle amount, is displayed on the display unit 16 in the form of a table, as shown in FIG. 9a. If depressing the print key, here, the answer of the step S35 is "Yes" to proceed to end the subroutine. Then the routine returns to step S19 in FIG. 3 and the printing process is performed in step S20. If the print key is not depressed, however, the subroutine proceeds to step S36 where the decision is made whether a display termination key is depressed or not. If not, the subroutine returns to step S31, but if so, the subroutine is finished.

Figure 9B:
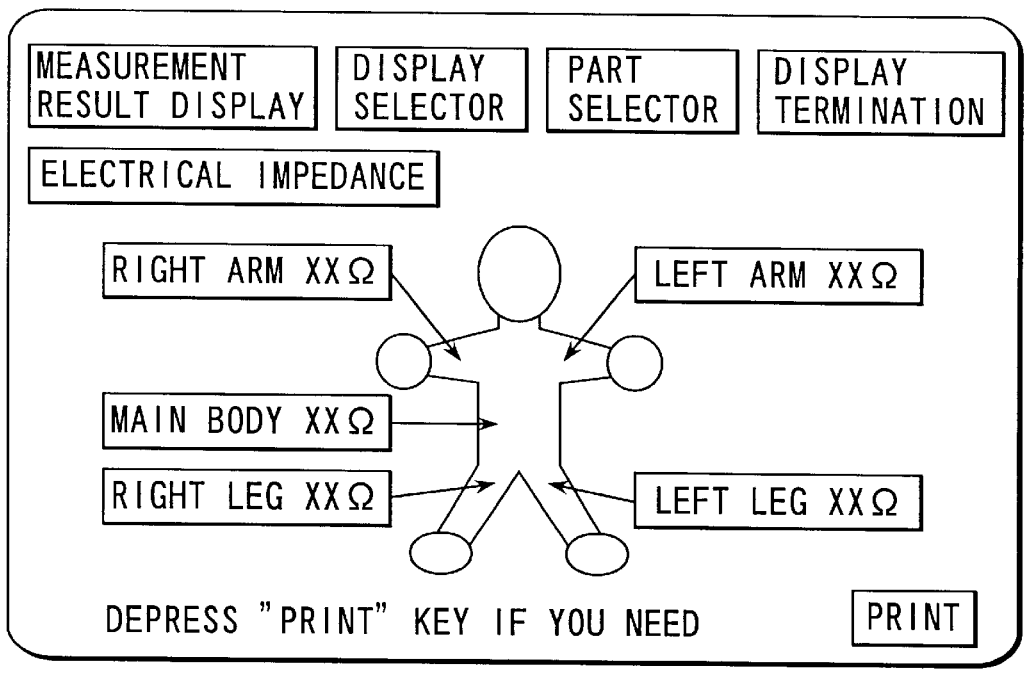

If the display selector switch is depressed while displaying the numerical data, the answer of step S31 is "Yes". Then in step S32 the display counter is increased by "1" so that the answer of step S33 is "No" and the subroutine proceeds to step S37. In this step the answer thereof is "Yes" and then in step S38 the whole body model of the person under test and the electrical impedance for each of the parts are displayed on the display unit 16, as shown in FIG. 9b. Thereafter, in step S39, the data for parts of the person is displayed, as described latter. Then the subroutine returns to step S35.

Figure 9C:
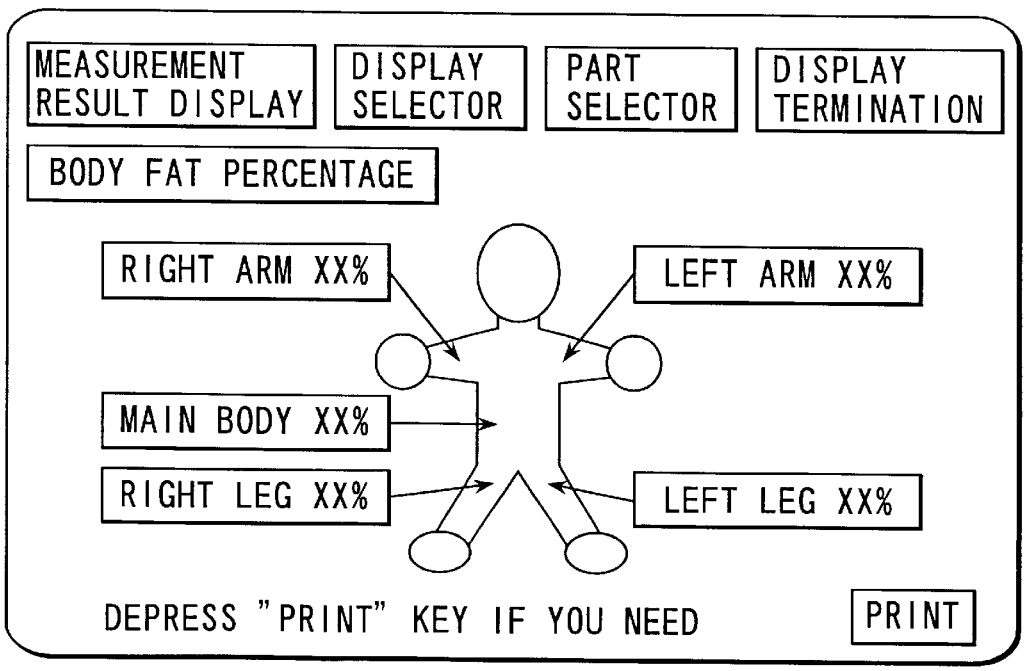

If the display selector switch is depressed while displaying the electrical impedance in this manner, the subroutine proceeds from step S31 via steps S32, S33, S37 to step S40. The answer of step S40 is "Yes" and the subroutine proceeds to step S41 where the whole body model of the person under test and the body fat percentage for each of the parts are displayed on the display unit 16, as shown in FIG. 9c. Then in step S42 the data for parts of the person is displayed, as in the case of step S39. Then the subroutine returns to step S35.

Figure 9D:
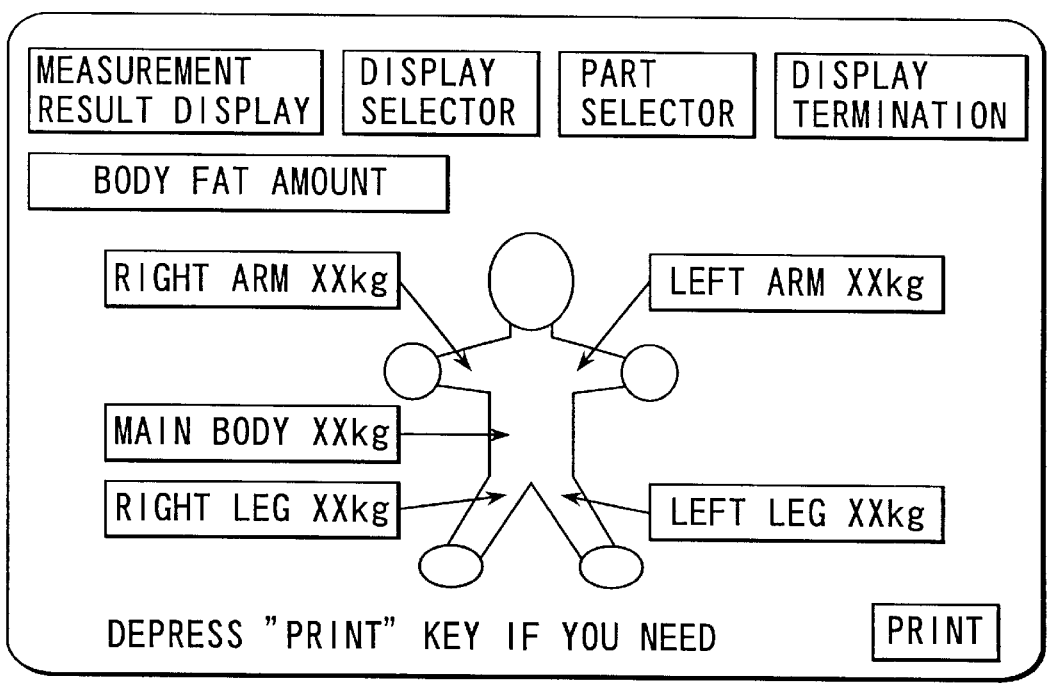

If the display selector switch is depressed while displaying the body fat percentage in this manner, the subroutine proceeds from step S31 via steps S32, S33, S37, S40 to step S43. The answer of step S43 is "Yes" and the subroutine proceeds to step S44 where the whole body model of the person under test and the body fat amount for each of the parts are displayed on the display unit 16, as shown in FIG. 9d. Then in step S45 the data for parts of the person is displayed, as in the case of step S39. Then the subroutine returns to step S35.

Figure 9E:
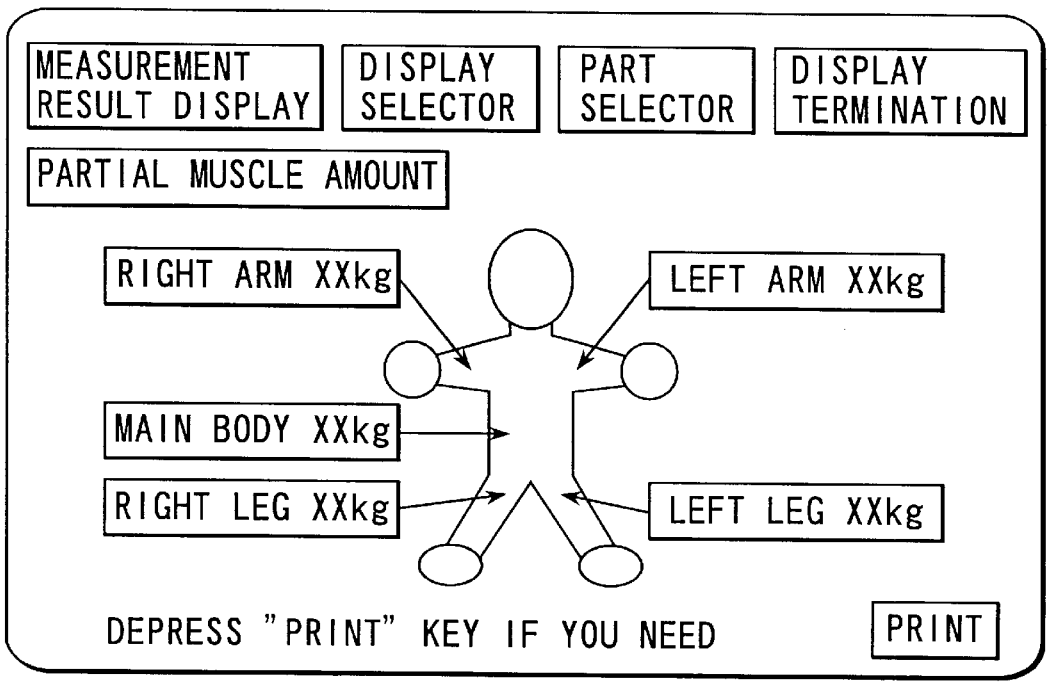

If the display selector switch is depressed while displaying the body fat amount in this manner, the subroutine proceeds from step S31 via steps S32, S33, S37, S40, S43 to step S46. The answer of step S46 is "Yes" and the subroutine proceeds to step S47 where the whole body model of the person under test and the partial muscle amount for each of the parts are displayed on the display unit 16, as shown in FIG. 9e. Then in step S48 the data for parts of the person is displayed, as in the case of step S39. Then the subroutine returns to step S35.

If the display selector switch is depressed while displaying the partial muscle amount in this manner, the subroutine proceeds from step S31 via steps S32, S33, S37, S40, S43, S46 to step S49. In this step the display counter is reset to "0" and then the subroutine returns to step S35. Because of the display counter being "0", the subroutine proceeds from step S33 to step S34 for numerical data display.

Figure 5:
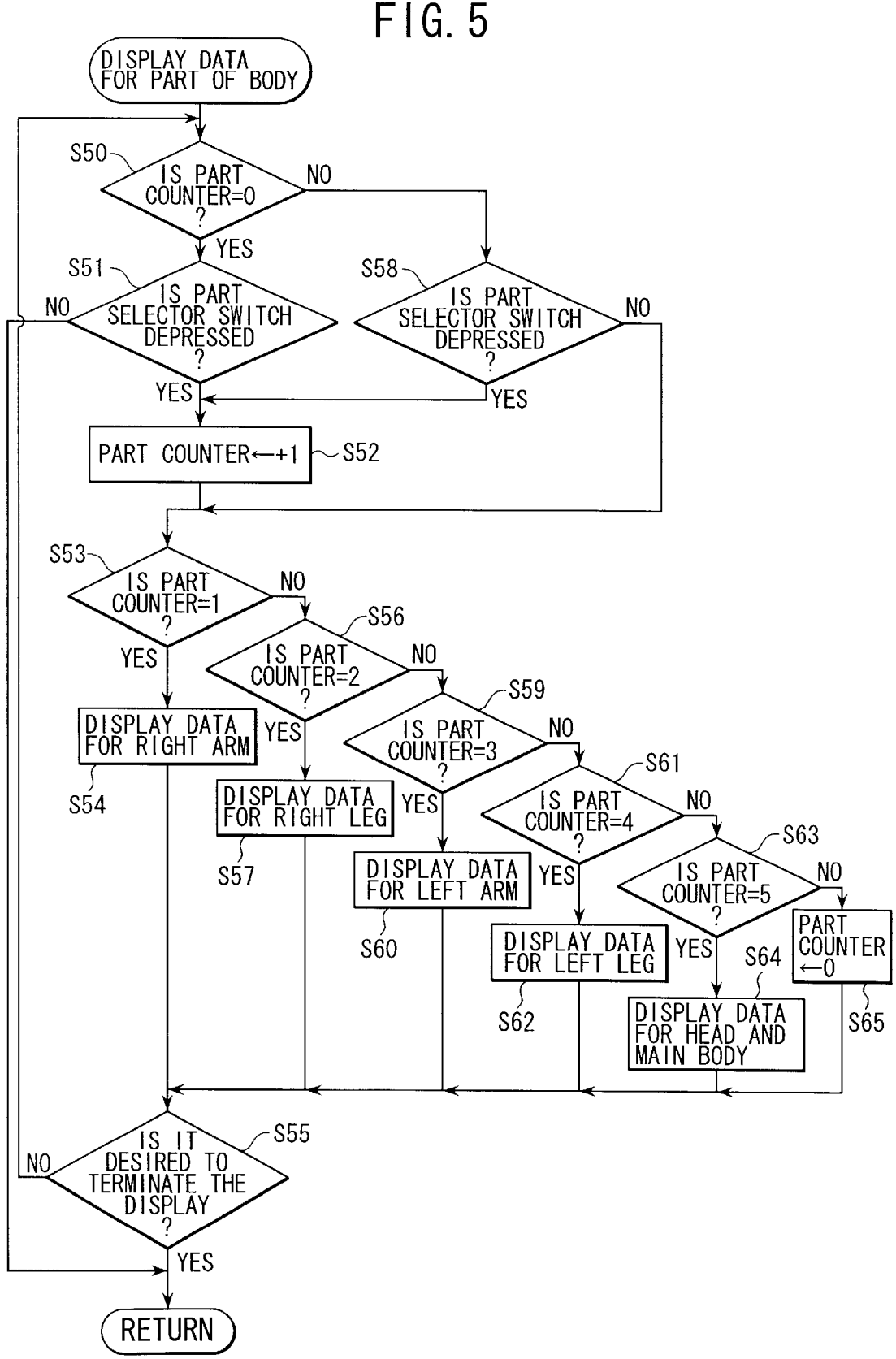
Figure 10A:
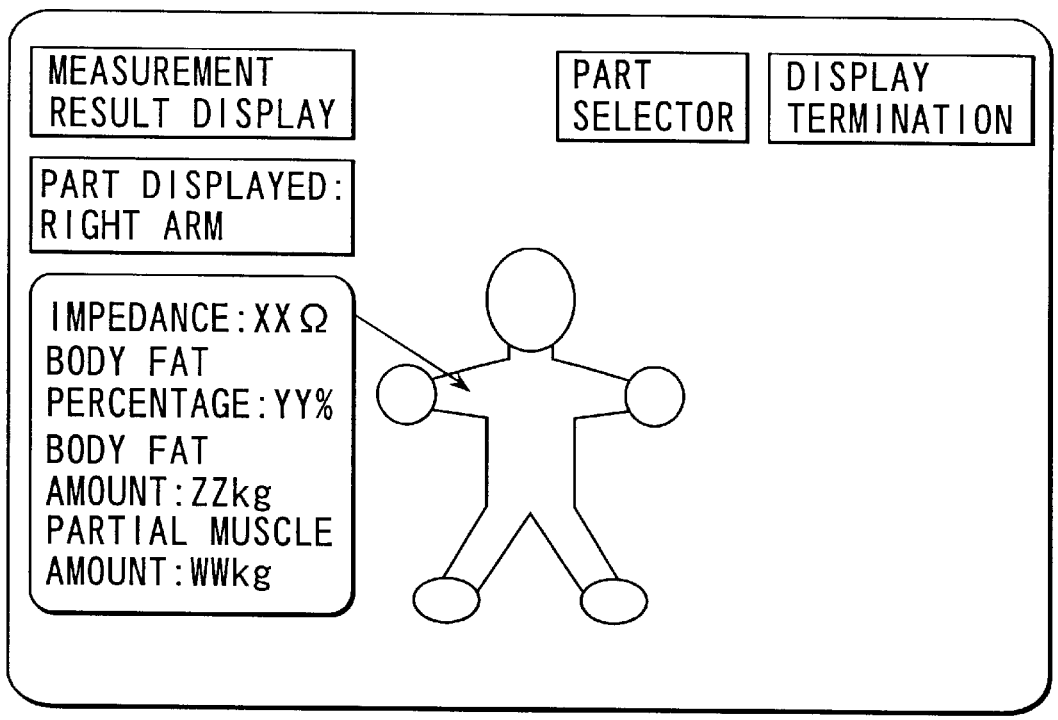

FIG. 5 shows the subroutine executed in each of steps S39, S42, S45 and S48 in FIG. 4 wherein each step has the same function to display the data for parts of the person. In step S50 the decision is made whether a part counter within the control unit 13 as shown in FIG. 2 is at "0" or not. Initially or after power up of the apparatus the part counter is at the initial value or "0" and then the answer of the step S50 is "Yes". Then the subroutine proceeds to step S51 where the decision is made whether a part selector switch as shown in FIG. 9 is depressed or not. If not, the subroutine returns to step S35 in FIG. 4. However, if the part selector switch is depressed in step S51, then the answer thereof is "Yes" and the subroutine proceeds to step S52 where the part counter is incremented by "1". In step S53 because of the part counter being "1" the answer thereof is "Yes" and the subroutine proceeds to step S54. In this step the whole body model of the person under test and all the measurement data for the part, in this case the right arm, of the person are displayed on the display unit 16, as shown in FIG. 10a. Then in step S55 the decision is made whether the display termination key is depressed or not. If so, the subroutine returns to step S35 in FIG. 4. Otherwise the subroutine returns to step S50 for maintaining the display.

Figure 10B:
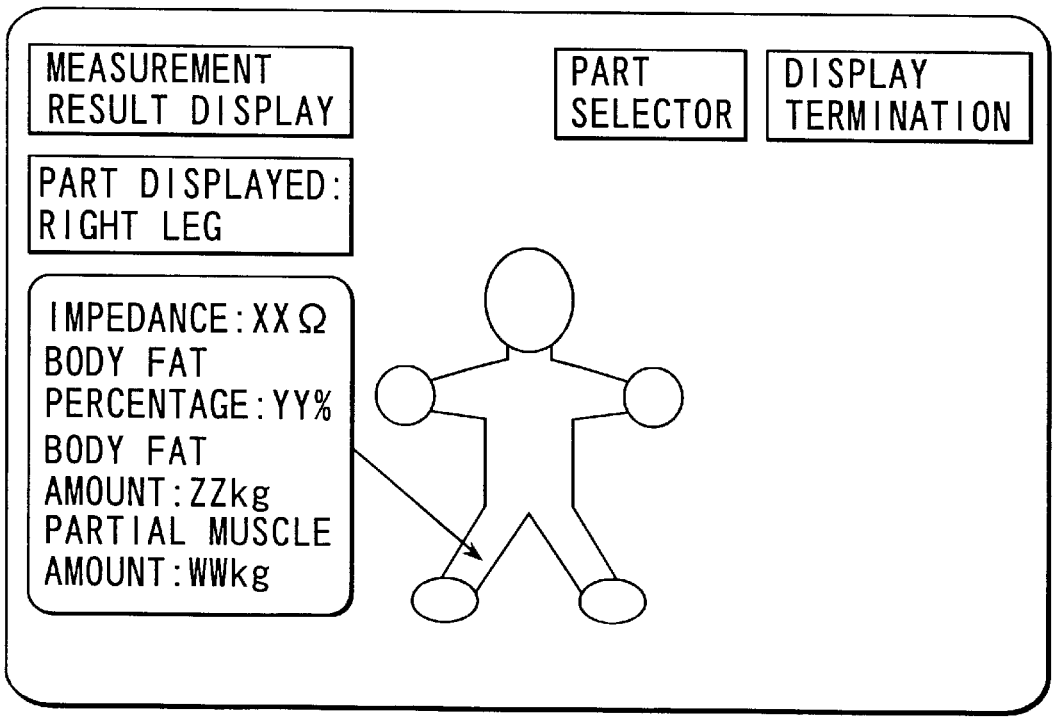
Figure 10C:
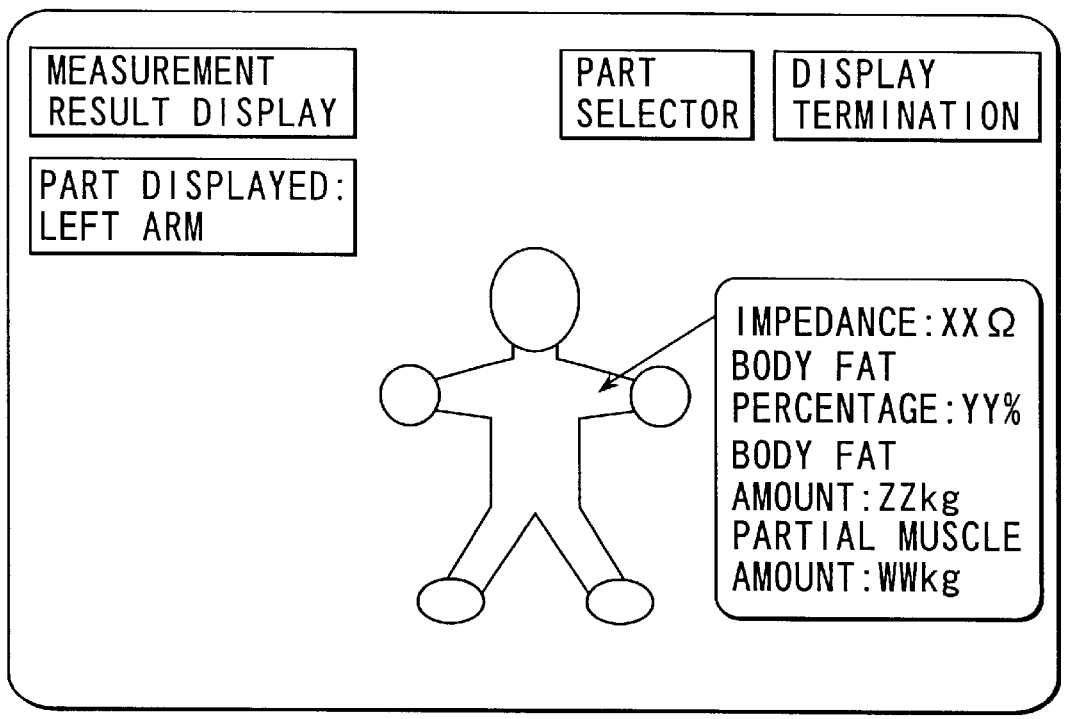

If the part selector switch is depressed while displaying the data for the right hand of the person, the answer of step S58 is "Yes". Then in step S52 the part counter is incremented to "2". At this moment the answer of step S53 is "No", but the answer to step S56 is "Yes". Therefore, the subroutine proceeds to step S57 where the whole body model of the person under test and all the measurement data for the part, in this case the right leg, of the person are displayed on the display unit 16, as shown in FIG. 10b. Then in step S55 the decision is made whether the display termination key is depressed or not. If so, the subroutine returns to step S35 in FIG. 4. Otherwise the subroutine returns to step S50 and repeatedly proceeds to steps S58, S53 and S56 for maintaining the display of the right leg of the person. If the part selector switch is depressed while displaying the data for the right leg of the person, the answer to step S58 is "Yes" and the subroutine proceeds to step S52 where the part counter is incremented by "1". Then the subroutine proceeds to steps S53, S56, S59, in turn, and in step S60 all the measurement data for the left arm of the person are displayed, as shown in FIG. 10c.

Figure 10D:
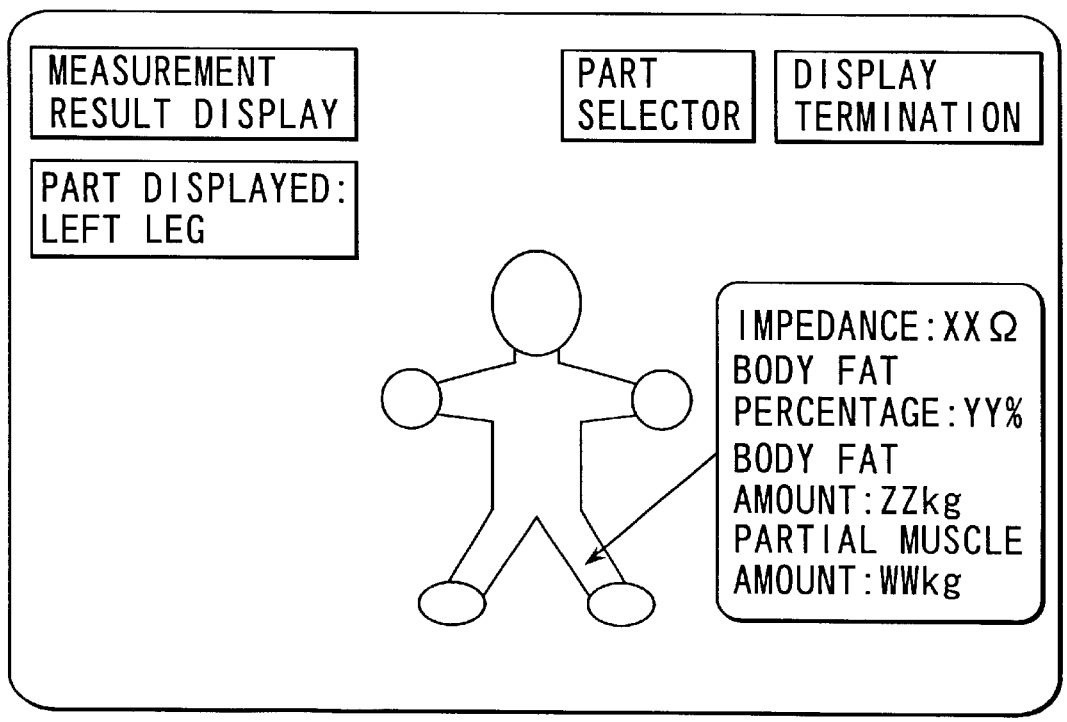
Figure 10E:
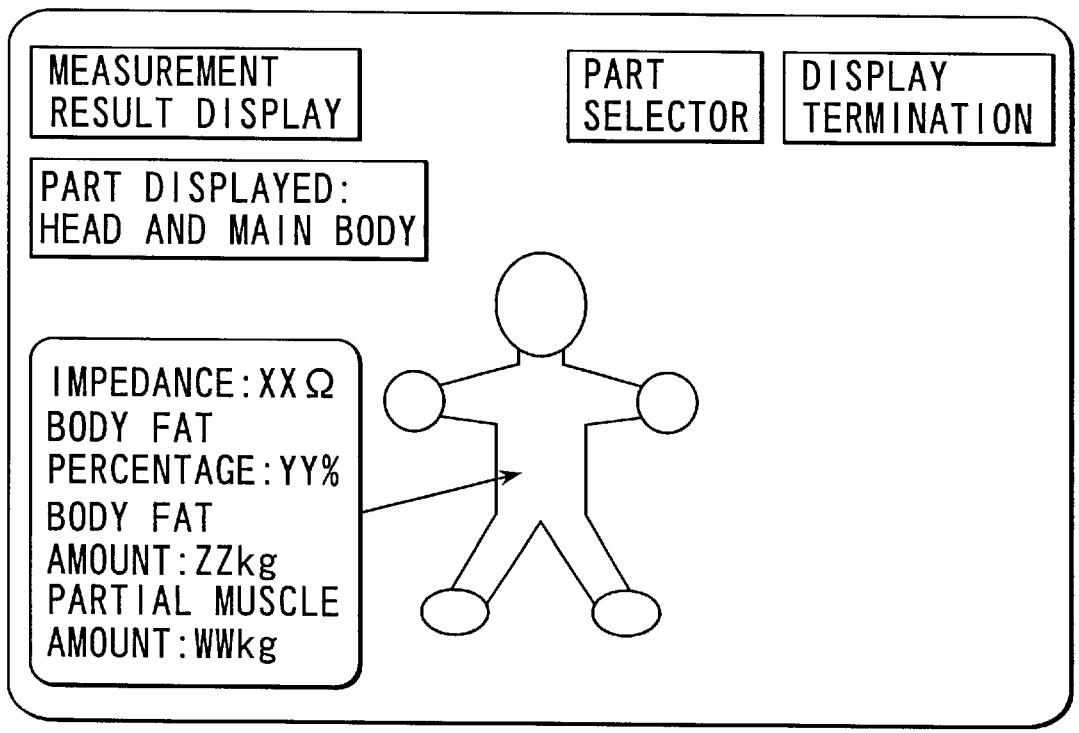

In the same manner the measurement data for the left leg, and the head and main body of the person under test are displayed, as shown in FIGS. 10d and 10e (see S61, S62, S64). If the part selector switch is depressed while displaying the data for the head and main body of the person, the answer of step S63 is "No" and the subroutine proceeds to step S65 where the part counter is reset to "0". Then the subroutine restores to the sequence in FIG. 4 via steps S55, S50 and S51.

In the embodiment as stated above the part of the body being measured at that moment (or the measuring path) is indicated by a broken line on the whole body model of the person under test. Alternatively the broken line may be moved in one way, like a telop, for helping to make the person unaware of how long the time has passed.

In the embodiment as shown in FIGS. 7a–7f and 8a–8e the point on the body into which the electrical current is introduced is indicated by the black dot and the point on the body on which the voltage is measured is indicated by the white dot. In addition the measuring path for part of the body is shown by the broken line. However in another embodiment only a current flowing path may be shown by a broken line. Or alternatively the measuring path and the current flowing path may be shown by the different types of lines.

FIG. Ha shows another embodiment in which the part of the body already measured is indicated by a solid line and the part being measured at that moment is indicated by a broken line. This clearly shows to the person under test the progress of the measurement.

Figure 11A:
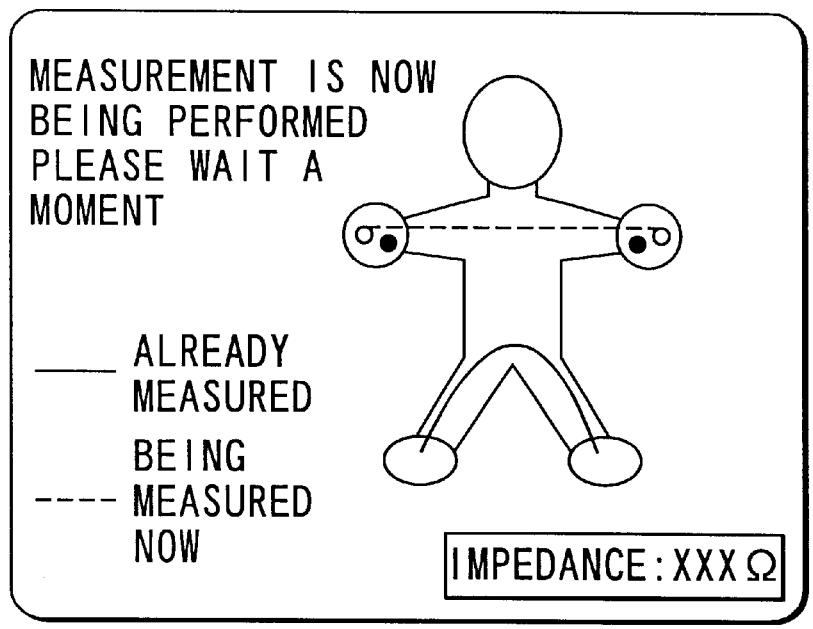
FIGS. 11a and 11b shows another embodiment of display screens of the display unit.
Figure 11B:
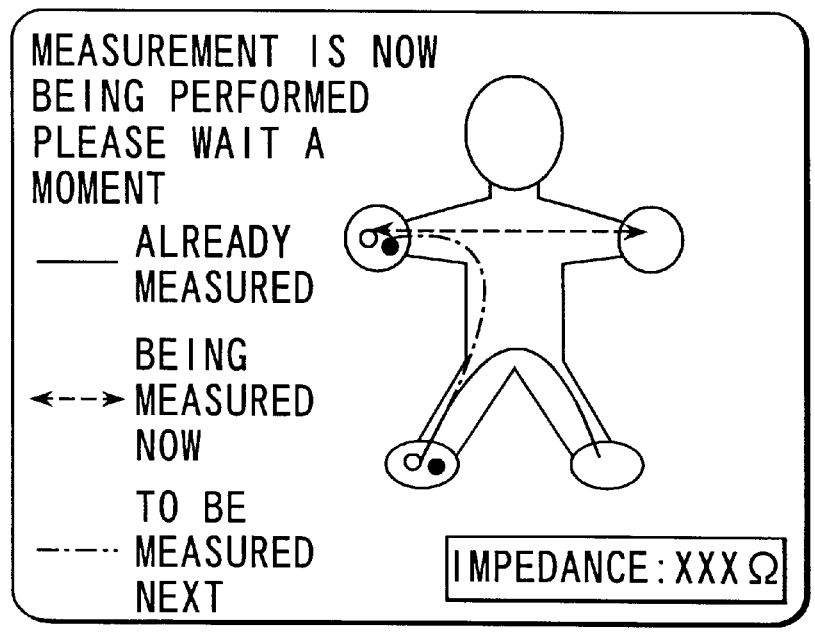
Figure 12A:
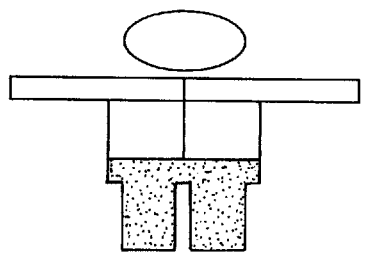
FIG. 12 shows further embodiment of display screens of the display unit.
Figure 12B:
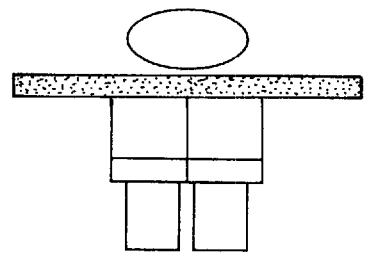
Figure 12C:
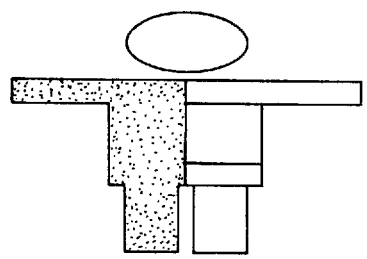
Figure 12D:
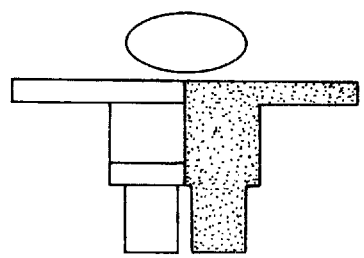
Figure 12E:
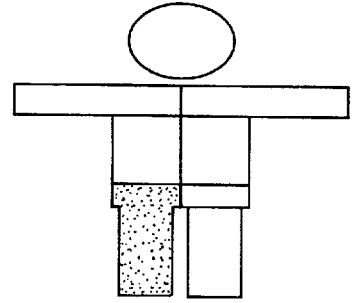
Figure 12F:
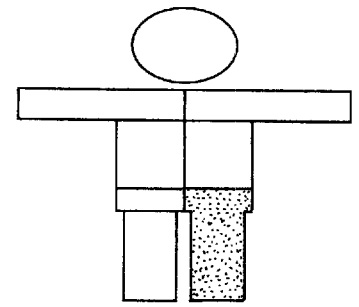
Figure 12G:
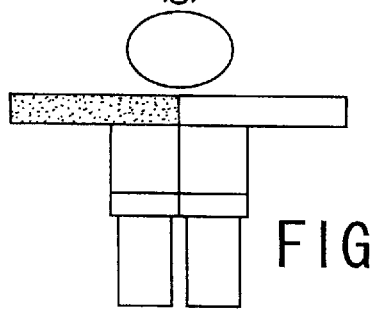
Figure 12H:
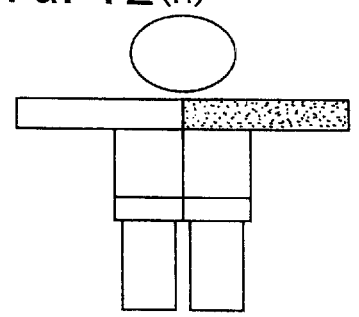
Figure 12I:
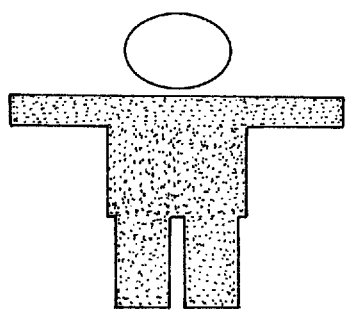

FIG. 11b shows further embodiment in which the part of the body already measured is indicated by a solid line, the part being measured at that moment is indicated by a double headed broken line, and the part to be measured next is indicated by a point-dot-line. This is more effective to make the person unaware of how long the time has passed.

FIGS. 12(a) to 12(i) show yet further embodiments in which the whole body model of the person under test is illustrated using a rectangular block for each of the measured parts and any block corresponding to the part being measured at that time has a dark shading. In this case the construction of display unit and the development of software can be simplified, as compared with the embodiments in FIGS. 7c to 8e.

In the embodiment as described above the measurement for nine (9) parts of the body has been described, by way of example. However, the present invention is not limited to such number of parts of the body, but it covers the case where less number of the parts of the body is measured. Furthermore, it is also within the scope of the present invention that a color display is used to more dearly show the progress of the measurement to the person under test.

It is apparent from the foregoing that the present invention has provided a new and improved measuring apparatus, comprising: a plurality of electrodes each of which is structured to make contact with a part of a living body; a current source connected to said electrodes; a voltage measuring unit connected to said electrodes; a control unit connected to said current source and said voltage measuring unit; and a display unit connected to said control unit, whereby said control unit instructs said display unit to display the part of the living body to which an electric current is fed by said current source via the associated electrodes.

The present invention is significantly effective in that a person under test can be afforded a sense of security because the person is made unaware of the time that has passed for the measurement and the person knows what part of the body is being measured at that time.

Further according to the present invention the part of the body already measured and the part of the body being measured at that time can be displayed. This can clearly indicate the progress of the measurement to the person under test.

Furthermore according to the present invention the part of the body already measured, the part of the body being measured at that time and the part of the body to be measured next can be displayed. This can made the person under test extremely unaware of the time that has passed for the measurement.

What is claimed is:

1. A living body measuring apparatus comprising:
    a plurality of electrodes each of which is structured to make contact with a part of a living body;
    a current source connected to said electrodes;
    a voltage measuring unit connected to said electrodes;
    a control unit connected to said current source and said voltage measuring unit; and
    a display unit connected to said control unit,
    wherein said control unit is for instructing said display unit to display the part of the living body to which an electric current is fed by said current source via the associated electrodes.

2. A living body measuring apparatus according to claim 1, further comprising a switching unit for selecting which electrodes the electric current is fed to.

3. A living body measuring apparatus according to claim 2, wherein the control unit is for changing the part of the body displayed on the display unit in response to the operation of said switching unit.

4. A living body measuring apparatus comprising:
    a plurality of electrodes each of which is structured to make contact with a part of a living body;
    a current source connected to said electrodes;
    a voltage measuring unit connected to said electrodes;
    a control unit connected to said current source and said voltage measuring unit; and
    a display unit connected to said control unit,
    wherein said control unit is for instructing said display unit to display the part of the living body of which voltage is measured by said voltage measuring unit on the associated electrodes.

5. A living body measuring apparatus according to claim 4, further comprising a switching unit for selecting the electrodes on which the voltage is measured.

6. A living body measuring apparatus according to claim 5 wherein the control unit is for changing the part of the body displayed on the display unit in response to the operation of said switching unit.

7. A living body measuring apparatus according to claim 1 or 4 wherein the parts of the living body that have already been measured, that are currently being measured, or that will be measured are displayed on the display unit with a solid line, a broken line or a point-dot-line.

8. A living body measuring apparatus according to claim 7 in which the parts of the living body that are currently being measured are displayed on the display unit with a broken line that moves one way.

9. A living body measuring apparatus according to claim 1 or 4 in which each part of the living body is displayed on the display unit in a rectangular block and the blocks corresponding to the parts that are currently being measured are displayed with a dark shading.

* * * * *